United States Patent
Tseng et al.

(10) Patent No.: US 9,822,713 B2
(45) Date of Patent: Nov. 21, 2017

(54) NETWORK BASED SHARING OF AUTOMATED FUEL CHARACTERISTICS

(71) Applicant: Ford Global Technologies, LLC, Dearborn, MI (US)

(72) Inventors: Fling Tseng, Ann Arbor, MI (US); Imad Hassan Makki, Dearborn Heights, MI (US); Pankaj Kumar, Dearborn, MI (US); Aed M. Dudar, Canton, MI (US); Robert Roy Jentz, Westland, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 0 days.

(21) Appl. No.: 15/006,272

(22) Filed: Jan. 26, 2016

(65) Prior Publication Data

US 2017/0211489 A1  Jul. 27, 2017

(51) Int. Cl.
| | | |
|---|---|---|
| F02D 19/08 | (2006.01) | |
| F02D 41/26 | (2006.01) | |
| F02D 41/00 | (2006.01) | |
| G01N 33/28 | (2006.01) | |

(52) U.S. Cl.
CPC ....... *F02D 19/087* (2013.01); *F02D 41/0032* (2013.01); *F02D 41/263* (2013.01); *G01N 33/2852* (2013.01); *F02D 2200/701* (2013.01)

(58) Field of Classification Search
CPC .. F02M 25/00; F02M 65/006; F02M 25/0818; G01M 3/025; F02D 2041/225; F02D 2200/0611; F02D 2041/1412; F02D 2200/0602; F02D 2200/0606; F02D 2200/701
See application file for complete search history.

(56) References Cited

U.S. PATENT DOCUMENTS

| | | |
|---|---|---|
| 5,868,117 A | 2/1999 | Moote et al. |
| 5,881,703 A | 3/1999 | Nankee, II et al. |

(Continued)

FOREIGN PATENT DOCUMENTS

| | | |
|---|---|---|
| CN | 201773084 U | 3/2011 |
| CN | 105604664 A | 5/2016 |

OTHER PUBLICATIONS

UK Search Report 16643P; GB Appl 1701274.1; dated Jun. 8, 2017; 3 pages.

*Primary Examiner* — Long T Tran
(74) *Attorney, Agent, or Firm* — Frank A. MacKenzie; Bejin Bieneman PLC

(57) ABSTRACT

A system of one or more computers configured to perform operations or actions by virtue of having software, firmware, hardware, or a combination of them installed on the system that causes the system to perform the actions. The programs can be configured to perform operations, when executed by computer, cause the computer to perform the actions. One general aspect includes a system, a program to initiate an evaporative control engine off natural vacuum test in a vehicle and identify a geolocation where a fuel was obtained for the vehicle. The system then determines an e100 value and an e0 value for a temperature of the fuel and determines a vehicle percentage of ethanol of the fuel using at least the e100 value, the e0 value, a timestamp, and a fuel tank pressure and adjusts at least one engine parameter based upon the percentage of ethanol of the first fuel.

20 Claims, 3 Drawing Sheets

(56) References Cited

U.S. PATENT DOCUMENTS

| | | | |
|---|---|---|---|
| 6,257,174 B1 | 7/2001 | Huff et al. | |
| 6,714,856 B2 | 3/2004 | Huff et al. | |
| 7,059,313 B2 * | 6/2006 | Lippa | F02P 5/1502 |
| | | | 123/518 |
| 8,706,383 B2 * | 4/2014 | Sauve | F02D 41/0025 |
| | | | 123/434 |
| 9,140,627 B2 * | 9/2015 | Dudar | F02M 65/00 |
| 2009/0171549 A1 | 7/2009 | Hyde et al. | |
| 2011/0162625 A1 * | 7/2011 | Espinoza | F02M 25/08 |
| | | | 123/521 |
| 2014/0379242 A1 | 12/2014 | Henein et al. | |
| 2015/0075251 A1 | 3/2015 | Jentz et al. | |
| 2015/0090006 A1 | 4/2015 | Peters et al. | |
| 2015/0219522 A1 * | 8/2015 | Tseng | F02M 25/0809 |
| | | | 701/102 |
| 2015/0354480 A1 * | 12/2015 | Dudar | F02D 41/0032 |
| | | | 701/22 |
| 2015/0369150 A1 * | 12/2015 | Dudar | F02M 25/0836 |
| | | | 123/519 |

\* cited by examiner

NETWORK BASED SHARING OF AUTOMATED FUEL CHARACTERISTICS

BACKGROUND

Autonomous or partially autonomous vehicles relieve drivers of various driving-related tasks. Such vehicles could use gasoline/ethanol fuel blends. An occasional operator or occupant of such a vehicle may not be able to identify degradation of the vehicle's engine performance due to a misrepresented percentage of the ethanol blend of the fuel. A fuel station, for example, may report that the fuel it is supplying is fifteen percent ethanol, but in actuality the fuel may be twenty percent ethanol. This misrepresentation could cause a vehicle's engine computer to operate the engine using an erroneous value for the ethanol percentage, which can degrade performance and/or damage the engine.

DETAILED DESCRIPTION

Fuel System Components

Figure 1:
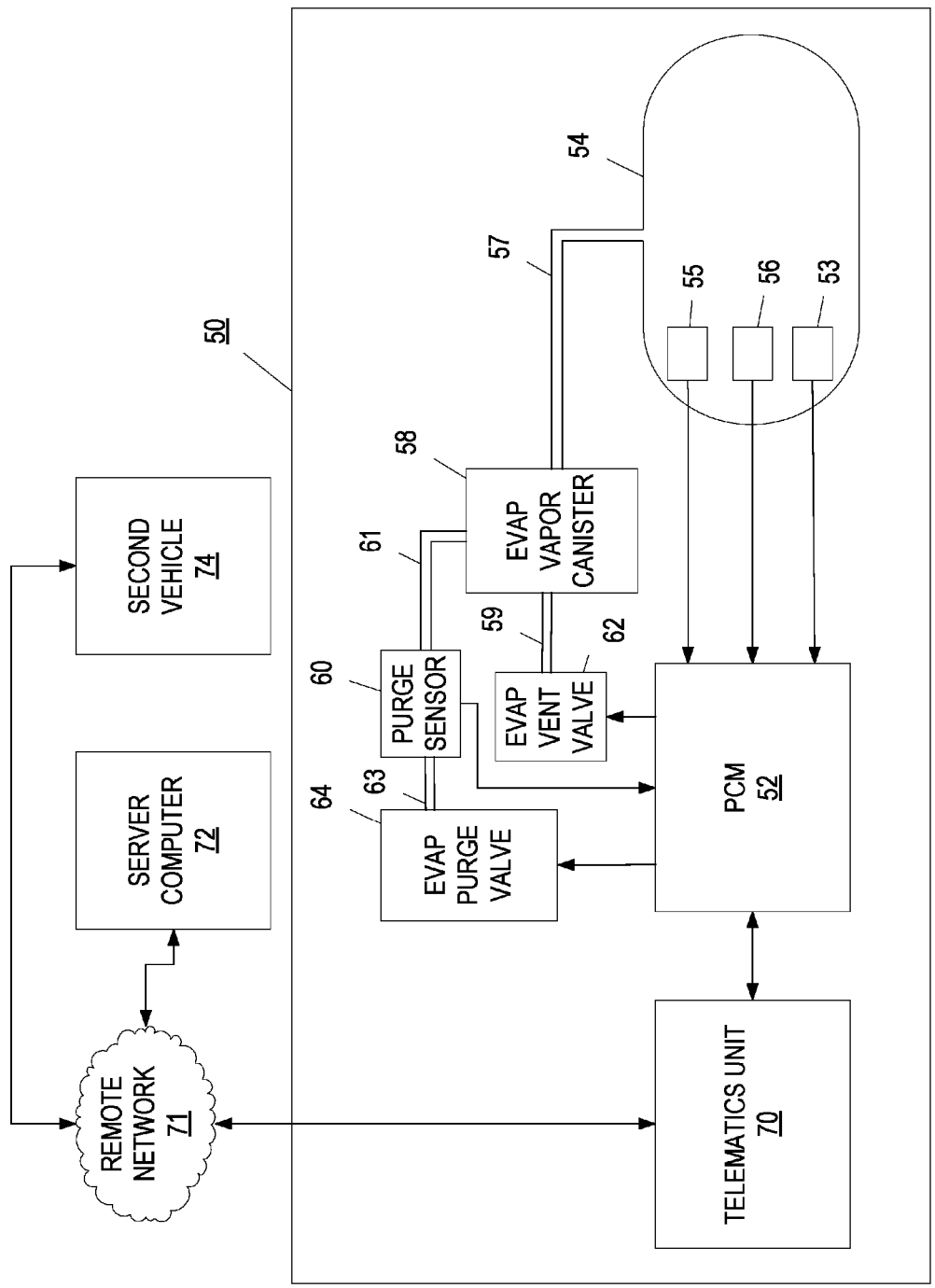
FIG. 1 is an exemplary schematic diagram illustrating the components of a vehicle fuel system.

In the Figures, like numerals indicate like elements throughout the several views. FIG. 1 is a schematic diagram illustrating components in an exemplary vehicle fuel system. A powertrain control module (PCM) 52 is communicatively coupled to fuel system temperature sensor 53, a fuel level sensor 56 and a fuel tank pressure sensor 55, all located in a fuel tank 54. The PCM 52 is also communicatively coupled to an Evaporative Emission Control System (EVAP) vent valve 62, a purge sensor 60 and an EVAP purge valve 64.

The PCM 52, as is known, typically contains a processor and a memory, the memory storing instructions executable by the processor. The PCM 52 memory (or another computing device in or communicatively coupled to a computing device on a vehicle communications bus) may also store various data, e.g., fuel ethanol levels, geolocation data of the fuel station (e.g., geo-coordinates such as longitude and latitude as determined by a Global Positioning System (GPS) or like navigation system in a vehicle 50), as well as gasoline vapor gas pressure values for an E0 fuel and an E100 fuel, which are explained below. The PCM 52 can be a combination of two or more computing modules such as are known, e.g., an engine control unit (ECU) and a transmission control unit (TCU).

The PCM 52 can also be communicatively coupled to a telematics unit 70 to communicate via a remote network 71, a server computer 72, and/or one or more second vehicle 74. The telematics unit 70 can be an embedded system on board a vehicle 50 that controls the communications and the tracking of the vehicle 50. The remote network 71 can include radio or other communications methodologies between the vehicle 50 and the server computer 72. The remote network 71 may be one or more digital networks such as are known, e.g., including the Internet or other packet networks and/or known wired or wireless technologies.

The server computer 72 typically includes a processor and a memory, the memory storing instructions executable by the processor. The server computer 72 memory may also store various data, e.g., fuel ethanol levels, geolocation data of the fuel stations, as well as the gasoline vapor gas pressure values for fuel types such as known E0 and E100 fuels.

The fuel system temperature sensor 53 sends a temperature value to the PCM 52. The fuel system temperature sensor 53 can be located in the fuel tank 54, attached to the surface of the fuel tank 54, or adjacent to the fuel tank 54. The fuel tank pressure sensor 55 can monitor the fuel tank 54 pressure to determine if there is an evaporation leak in the fuel system that would allow unburned fuel vapor into the atmosphere. Due to temperature variations, the fuel tank pressure in a sealed fuel tank can generate pressures in excess of positive 25 kilopascals (kPa) or approach a vacuum at less than 5 kPa.

The fuel level sensor 56 detects an amount of fuel in the fuel tank 54 and sends a fuel level to the PCM 52. The fuel tank pressure sensor 55 fuel tank pressure sensor is part of the evaporative emission control system.

A vent line 57 connects the fuel tank 54 to the EVAP vapor canister 58. The EVAP vapor canister 58 is also connected to a purge sensor 60 via first purge line 61 and to an EVAP vent valve 62 via an EVAP line 59. The EVAP vapor canister 58 purpose is to keep gasoline from evaporating into the atmosphere. The fumes from the fuel tank 54 flow into the EVAP vapor canister 58 which contains activated carbon and is therefore capable of adsorbing the fuel vapor. The purge sensor 60 is also connected to an EVAP purge valve 64 via a purge line 63.

When a vehicle engine is running, the fuel vapors can be purged from the EVAP vapor canister 58 and burned inside the engine. The EVAP purge valve 64 precisely controls the amount of fuel vapor that is purged from the EVAP vapor canister 58. The EVAP purge valve 64 has an electrically-operated solenoid that is controlled by the PCM 52. When the engine is off, the EVAP purge valve 64 valve is closed. When the engine is running and fully warmed up, the PCM 52 gradually opens the EVAP purge valve 64 to allow some amount of fuel vapor to be moved from the EVAP vapor canister 58 to be burned in the engine. The purge flow is monitored by the purge sensor 60, for example, if the purge flow is less or more than is expected under the conditions, the PCM 52 will illuminate a "Check Engine" light.

The EVAP vent valve 62 controls the flow of outside air in and out of the EVAP vapor canister 58 and prevents outside air from entering the EVAP system during an evaporative system leak test. One side of the EVAP vent valve 62 is connected to the EVAP vapor canister 58. Another side of the valve 62 is connected to the vent hose (not shown) that may have a filter or screen at a hose end to keep out foreign objects and dirt. The EVAP vent valve 62 is controlled by the PCM 52. Normally the EVAP vent valve 62 is open and closes when the PCM 52 tests the EVAP system for leaks; for example, if a leak in the EVAP system is detected, the "Check Engine" light or the like will illuminate on the dash and the trouble code related to the problem will be stored in the engine computer.

Engine Off Natural Vacuum (EONV) Test

Figure 2:
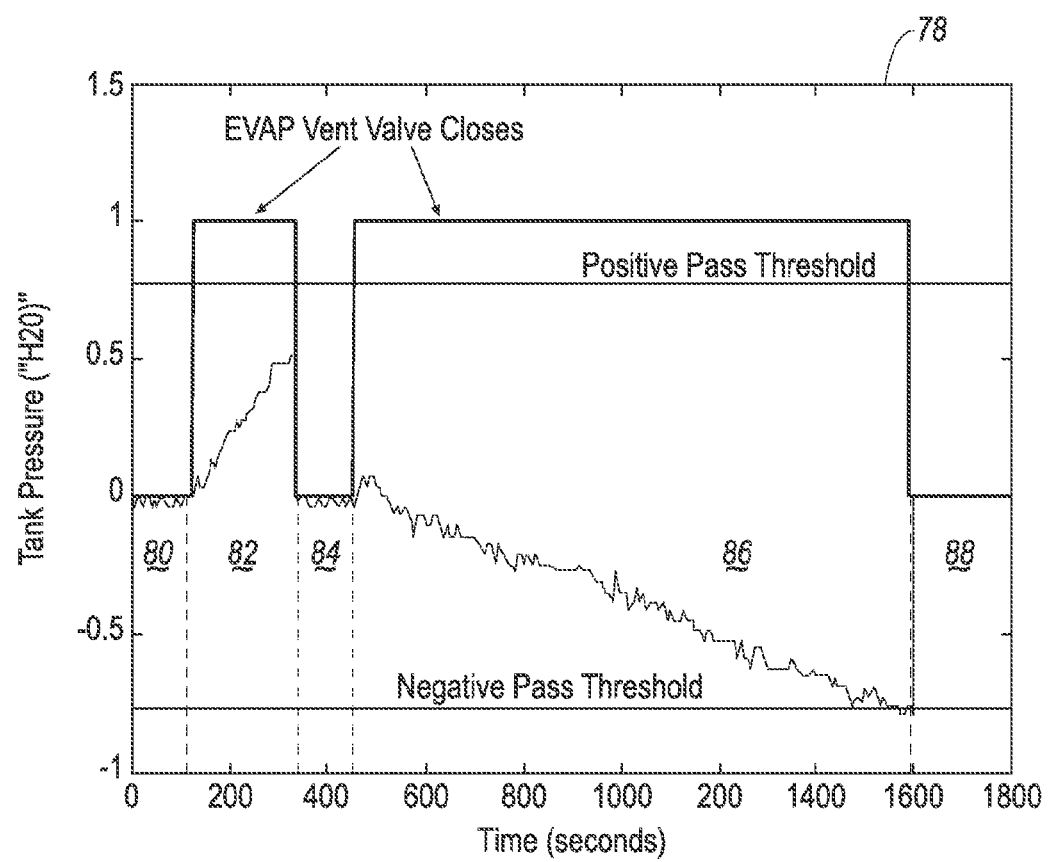
FIG. 2 is a plot of an exemplary engine off natural vacuum (EONV) test.

Now with reference to FIGS. 1 and 2, the EONV typically test runs after the ignition is turned off as shown in section 80 of a graph 78 (FIG. 2). The pressure test begins by closing the EVAP vent valve 62 and observing the pressure increase inside the fuel tank 54 with the fuel tank pressure sensor 55 as shown in section 82. At this point, the fuel is still warm enough for some amount of vaporization to occur. If the pressure increase reaches a pressure threshold as determined by the fuel tank pressure sensor 55, the diagnostic test passes, meaning the system is leak-free, and the test is over. The pressure threshold is a function of predicted ambient temperature and fuel level.

If the pressure threshold is not reached, the PCM 52 records the peak pressure that is reached, and sets up a vacuum threshold for a vacuum test. Then, the PCM 52 opens the EVAP vent valve 62 and waits for system pressure to bleed down as shown in a section 84 of the graph 78.

During vacuum testing, the PCM 52 closes the canister vent valve and monitors the tank 54 vacuum to determine if the vacuum threshold is reached by reading the fuel tank pressure sensor 55 as shown in a section 86 of the graph 78. If the vacuum threshold is reached, indicating that the system can hold a vacuum, the diagnostic passes, and the test is complete as shown in a section 88. If the vacuum threshold is not reached, the PCM 52 can consider the test a "fail."

The PCM 52 stores the EVAP EONV result and the EVAP EONV data in a database, e.g., the EVAP EONV result would be either a pass or fail of the EVAP EONV test. The EVAP EONV data could include a final tank vapor pressure reading, a date and time stamp, whether the positive pressure of the negative pressure were performed and periodic tank vapor pressure values obtained during the EVAP EONV test. The negative pressure test is also known as a vacuum pressure test. If the fuel system cannot reach a certain threshold, the test fails and the PCM 52 will switch on a malfunction indicator lamp, indicating a leak larger than 0.020-inch (0.51 mm).

Dalton's Law

In chemistry and physics, Dalton's law (also called Dalton's law of partial pressures) states that in a mixture of non-reacting gases, the total pressure exerted is equal to the sum of the partial pressures of the individual gases. In other words, if the gas vapor pressure of the gasoline is added to the gas vapor pressure of the ethanol, it will equal a total fuel tank vapor pressure. For example, the fuel has a mixture of 85% gasoline and 15% ethanol. The vapor pressures of the gasoline and the ethanol will also approximately equal the same percentages as illustrated in Equation (1), where $P_A X_A$ is a first gas vapor pressure, e.g., ethanol, and $P_B X_B$ is a second gas vapor pressure, e.g., gasoline. $P_A$ is the amount of ethanol vapor gas (also known as number of moles) and $X_A$ is a constant derived from experiments. $P_B$ is the amount of gasoline vapor gas (also known as number of moles) and $X_b$ is also constant derived from experiments.

$$\text{Total Fuel Tank Vapor Pressure} = P_A X_A + P_B X_B \quad \text{Equation (1)}$$

When the constants $X_A$ and $X_B$ are added together, there sum is one. Therefore, $X_B$ is equal to one minus $X_A$, as illustrated in Equation (2).

$$X_B = 1 - X_A \quad \text{Equation (2)}$$

Fuel Blending

Ethanol fuel mixtures, as is known, have "E" numbers which describe the percentage of ethanol fuel in the mixture by volume, for example, E85 is 85% anhydrous ethanol and 15% gasoline. Intermediate ethanol and gasoline blends can be represented as mixture of E0 and E100. For example, E10 can represent a blend of 10% ethanol (E100) and 90% gasoline (E0). Substituting from Equation (1), the vapor pressure of E10 can be written as Equation (3), where $P_{E10}$ is the Total Fuel Tank Vapor Pressure, $P_{E100}$ is the amount of ethanol vapor gas and $P_{E0}$ is the amount of gasoline vapor gas. In other words, the pressure of $P_{E10}$ is equal to 10 percent of the ethanol vapor gas added to 90 percent of the gasoline vapor gas pressure. The values for $P_{E100}$ and $P_{E0}$ are known from experimental values.

$$P_{E10} = P_{E100}*0.1 + P_{E0}*0.9 \quad \text{Equation (3)}$$

Equation (4) can be used to deduce a percentage of ethanol of a fuel mixture, where $P_{Ey}$ is the current vapor pressure as measured from the EONV test and y represents the percentage of ethanol.

$$P_{Ey} = P_{E100}*y + P_{E0}*(1-y) \quad \text{Equation (4)}$$

In a positive pressure example, after the EONV test ends, the fuel tank pressure sensor 55 indicates a pressure of 20 Kpa at the fuel tank 54. From this pressure reading, a value "y" representing the percentage of ethanol can be calculated. At 20 degrees centigrade, it has been determined that $P_{E100}$ has a value of 14.35 and the $P_{E0}$ has a value of 52. These values are inserted into Equation (4) and solved for y, as shown in Equation (5). In this example, it is determined that y is equal to 84.99, which indicating the "E" value of the fuel is E85, or 85% ethanol.

$$20 = 14.35*y + 52*(1-y) \quad \text{Equation (5)}$$

In a negative pressure example, after the EONV test ends, the fuel tank pressure sensor 55 indicates a pressure of –2 Kpa at the fuel tank 54. From this pressure reading, a value for the percentage of ethanol, "y" can be calculated. At 0 degrees centigrade, it has been determined that $P_{E100}$ has a value of –47 and the $P_{E0}$ has a value of 103. It is simply a matter of inserting these value into Equation (4) and solving for y, as shown in Equation (6). After performing the algebra, it is determined that y is equal to 70.0, which means the "E" value of the fuel is "E70."

$$-2 = -47.0*y + 103*(1-y) \quad \text{Equation (6)}$$

With the percentage of ethanol value determined, the vehicle PCM 52 can better accommodate for the differences in the reported percentage ethanol level and the determined ethanol level. For example, a fuel station located at a first geographic location could report that its fuel is E70, or 70% ethanol to 30% gasoline. The vehicle 50 can determine through the above EONV test that the fuel is actually E85, or 85% ethanol and 15% gasoline. As discussed above, the unreported additional alcohol may cause engine performance issues or even damage the engine.

Geo-Locating Fuel Stations

Since the fuel station geolocation is known, the vehicle 50 can detect any discrepancies between the reported ethanol rating and its determined ethanol rating. The determined rating can be uploaded to the server 72 via the telematics unit 70 and the remote network 71, and stored in a database. For example, the information can include a timestamp, the geolocation of the fuel station, the reported percentage of ethanol in the fuel and the determined percentage of ethanol in the fuel.

Once the server 72 has the above information, the fuel characteristics can be available to other vehicles by a query of the database permitting other vehicles the ability to obtain the ethanol percentage before filling up. Once a second vehicle 74 has the fuel information, the second vehicle 74 can obtain fuel at the fuel station and compensate for the variance in ethanol percentages or choose another fuel station with a more reliable ethanol percentage reporting.

Additionally, the second vehicle 74 can also perform the EVAP EONV test and determine the ethanol percentage and upload its results to the server 72. For example, the information can include a timestamp, the geolocation of the fuel station, the reported percentage of ethanol in the fuel and the determined percentage of ethanol in the fuel. The server 72, which has a database of reported ethanol percentages as they relate to the first fuel station, can determine an average of ethanol percentages as reported by various vehicles. For example, the first vehicle reports that the ethanol percentage is 80% and the second vehicle 74 reports the ethanol percentage is 85% for the E85 fuel. The server 72 can determine that the average reported ethanol percentage is 82.5%.

In another example, the server 72 can determine that a second geo-located fuel station may constantly state that their fuel is E70, but from collected reports from various vehicles, the fuel is determined to be E85. When the vehicle 50 queries the server 72 with regards to the second fuel station's reporting versus the determined percentage of ethanol, the server 72 can indicate in its response to the query that the ethanol to gasoline blend reporting has been inconstant over a determined time period.

Process Flow

Figure 3:
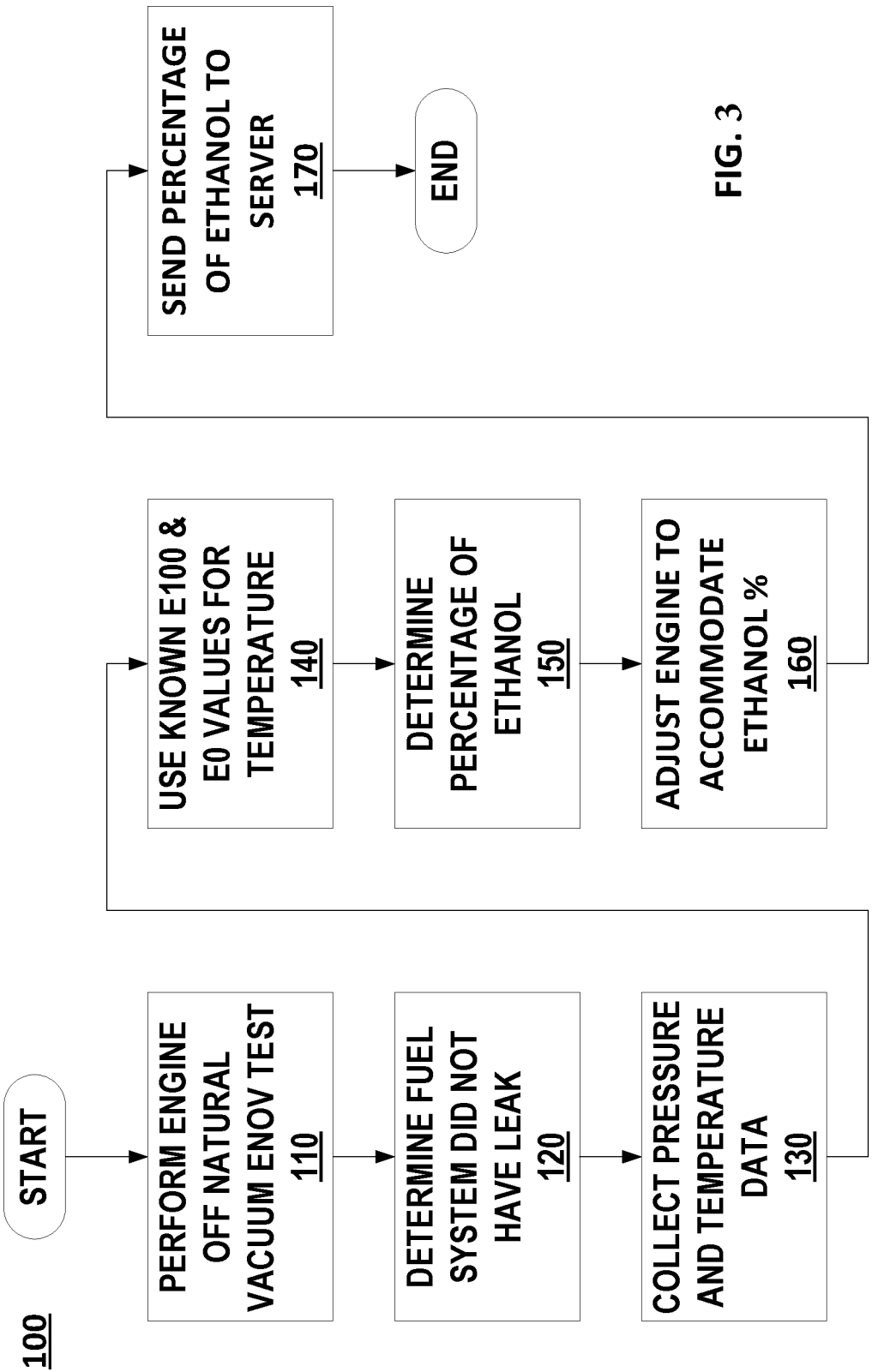
FIG. 3 is a flowchart of an exemplary process that may be implemented by the vehicle's ethanol fuel assessment system of FIG. 1.

FIG. 3 is a flow chart illustrating an exemplary process 100 of the system that may be implemented by a computer, e.g., the PCM 52, in an autonomous or semiautonomous vehicle 50.

The process 100 begins in a block 110, in which a vehicle 50, e.g., via the PCM 52, performs an engine-off natural vacuum test looking for ways fuel vapor can escape the fuel system. In addition to leak detection, a monitoring of the fuel tank 54 pressure and temperature allows the determination of the ethanol to gasoline ratio at the completion of a successful test. The EONV test procedure is known and has been described above.

Next, in a block 120, the PCM 52 determines that the fuel system either (a) passed the positive pressure test or the negative pressure test or (b) the fuel system has a leak and has failed the test. If the fuel system has a leak, the process 100 ends.

Next, in a block 130, the PCM 52 collects the fuel tank 54 pressure and temperature.

Next, in a block 140, the system 100 looks up in a memory of the PCM 52 the values for E100 and E0 at their current temperature. Alternatively, the PCM 52 can request the values from the server 72 if the values are not already locally stored in the PCM 52.

Next, in a block 150, the PCM 52 determines the percentage of ethanol using Equation (4) and solving for "y." See examples above.

Next, in a block 160, the PCM 52 adjust at least one engine parameter based upon the determined ethanol to gasoline level. For example, one or more of the engine spark timing, the fuel injector timing, as well as the air to fuel mixture, can be adjusted for improved performance.

Next, in a block 170, the "E" value and the location of the fuel station is sent to the server 72 to be stored in a database which will allow other vehicles to obtain a current "E" rating of that particular fuel station. Following the block 170, the process 100 ends.

Conclusion

As used herein, the adverb "substantially" modifying an adjective means that a shape, structure, measurement, value, calculation, etc. may deviate from an exact described geometry, distance, measurement, value, calculation, etc., because of imperfections in the materials, machining, manufacturing, sensor measurements, computations, processing time, communications time, etc.

Computing devices such as those discussed herein generally each include instructions executable by one or more computing devices such as those identified above, and for carrying out blocks or steps of processes described above. Computer executable instructions may be compiled or interpreted from computer programs created using a variety of programming languages and/or technologies, including, without limitation, and either alone or in combination, Java™, C, C++, C#, Visual Basic, Java Script, Perl, HTML, PHP, etc. In general, a processor (e.g., a microprocessor) receives instructions, e.g., from a memory, a computer readable medium, etc., and executes these instructions, thereby performing one or more processes, including one or more of the processes described herein. Such instructions and other data may be stored and transmitted using a variety of computer readable media. A file in a computing device is generally a collection of data stored on a computer readable medium, such as a storage medium, a random access memory, etc.

A computer readable medium includes any medium that participates in providing data (e.g., instructions), which may be read by a computer. Such a medium may take many forms, including, but not limited to, non-volatile media, volatile media, etc. Non-volatile media include, for example, optical or magnetic disks and other persistent memory. Volatile media include dynamic random access memory (DRAM), which typically constitutes a main memory. Common forms of computer readable media include, for example, a floppy disk, a flexible disk, hard disk, magnetic tape, any other magnetic medium, a CD ROM, DVD, any other optical medium, punch cards, paper tape, any other physical medium with patterns of holes, a RAM, a PROM, an EPROM, a FLASH EEPROM, any other memory chip or cartridge, or any other medium from which a computer can read.

With regard to the media, processes, systems, methods, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of systems and/or processes herein are provided for the purpose of illustrating certain embodiments, and should in no way be construed so as to limit the disclosed subject matter.

Accordingly, it is to be understood that the above description is intended to be illustrative and not restrictive. Many embodiments and applications other than the examples provided would be apparent to those of skill in the art upon reading the above description. The scope of the invention should be determined, not with reference to the above description, but should instead be determined with reference to claims appended hereto and/or included in a non-provisional patent application based hereon, along with the full scope of equivalents to which such claims are entitled. It is anticipated and intended that future developments will occur in the arts discussed herein, and that the disclosed systems and methods will be incorporated into such future embodiments. In sum, it should be understood that the disclosed subject matter is capable of modification and variation.

What is claimed is:

1. A system, comprising a computer having a processor and a memory, the memory storing instructions executable by the processor such that the computer is programmed to:

actuate a valve to initiate an evaporative control (EVAP) engine off natural vacuum (EONV) test in a first vehicle;

identify a first geolocation where a first fuel was obtained for the first vehicle;

receive sensor data to determine an E100 value and an E0 value for a first temperature of the first fuel;

determine a first vehicle percentage of ethanol of the first fuel using at least the E100 value, the E0 value, a timestamp, and a fuel tank pressure; and adjust in the computer at least one engine parameter based upon the percentage of ethanol of the first fuel.

2. The system of claim 1, wherein the computer is further programmed to store at least the percentage of ethanol of the first fuel and the first geolocation in a database.

3. The system of claim 2, wherein at least an EVAP EONV result and a EVAP EONV data is stored in the database.

4. The system of claim 2, wherein the database is located on a server computer accessed via a network outside of the first vehicle.

5. The system of claim 4, wherein the computer is further programmed to request at least one of the E100 value and the E0 value from the server.

6. The system of claim 4, wherein the computer is connected to a remote network via a first vehicle telematics unit.

7. The system of claim 4, wherein the server computer is further programmed to receive at least a second vehicle percentage of ethanol and a second EVAP EONV test data from a second vehicle at the first geolocation;

determine an average percentage of ethanol for the first geolocation from the first vehicle percentage of ethanol and the second vehicle percentage of ethanol; and store the average percentage of ethanol in the database.

8. The system of claim 7, wherein the computer is further programmed to send a percentage of ethanol request to the server computer for the first geolocation and to adjust at least one engine parameter based upon a percentage of ethanol response.

9. The system of claim 1, wherein the EVAP EONV test is at least a positive pressure test and a negative pressure test.

10. The system of claim 1, wherein the computer is included in a powertrain control module (PCM).

11. A method, comprising:
initiating an evaporative control (EVAP) engine off natural vacuum (EONV) test in a first vehicle;

identifying a first geolocation where a first fuel was obtained for the first vehicle;

determining an E100 value and an E0 value for a first temperature of the first fuel;

determining a first vehicle percentage of ethanol of the first fuel using at least the E100, the E0, a timestamp, and a fuel tank pressure; and adjusting at least one engine parameter based upon the percentage of ethanol of the first fuel.

12. The method of claim 11, further comprising storing at least the percentage of ethanol of the first fuel and the first geolocation in a database.

13. The method of claim 12, wherein at least an EVAP EONV result and a EVAP EONV data is stored in the database.

14. The method of claim 12, wherein the database is located on a server computer accessed via a network outside of the first vehicle.

15. The method of claim 14, further comprising requesting at least one of the E100 value and the E0 value from the server.

16. The method of claim 14, further comprising:
receiving at least a second vehicle percentage of ethanol and a second EVAP EONV test data from a second vehicle at the first geolocation;

determining an average percentage of ethanol for the first geolocation from the first vehicle percentage of ethanol and the second vehicle percentage of ethanol; and storing the average percentage of ethanol in the database.

17. The method of claim 16, further comprising sending a percentage of ethanol request to the server computer for the first geolocation and adjusting at least one engine parameter based upon a percentage of ethanol response.

18. The method of claim 11, further comprising performing at least a positive pressure EVAP EONV test and a negative pressure EVAP EONV test.

19. The method of claim 11, further comprising executing the EVAP EONV test in a computer included in a powertrain control module (PCM).

20. The method of claim 19, wherein the computer is connected to a remote network via a first vehicle telematics unit.

* * * * *